United States Patent [19]

Chikama

[11] Patent Number: 4,721,099

[45] Date of Patent: Jan. 26, 1988

[54] OPERATING MECHANISM FOR BENDABLE SECTION OF ENDOSCOPE

[75] Inventor: Toshio Chikama, Tokyo, Japan

[73] Assignee: Kabushiki Kaisha Machida Seisakusho, Japan

[21] Appl. No.: 922,020

[22] Filed: Oct. 22, 1986

[30] Foreign Application Priority Data

| Oct. 30, 1985 | [JP] | Japan | 60-165697[U] |
| Oct. 30, 1985 | [JP] | Japan | 60-165698[U] |
| Oct. 30, 1985 | [JP] | Japan | 60-165699[U] |
| Nov. 11, 1985 | [JP] | Japan | 60-172320[U] |
| Dec. 10, 1985 | [JP] | Japan | 60-189054[U] |
| Aug. 25, 1986 | [JP] | Japan | 61-128284[U] |

[51] Int. Cl.⁴ .............................................. A61B 1/00
[52] U.S. Cl. ........................................ 128/4; 138/118
[58] Field of Search ................ 128/4, 6; 138/120, 118

[56] References Cited

U.S. PATENT DOCUMENTS

| 4,499,895 | 2/1985 | Takayama | 128/6 |
| 4,503,842 | 3/1985 | Takayama | 128/4 |
| 4,559,928 | 12/1985 | Takayama | 128/6 |
| 4,617,914 | 10/1986 | Ueda | 128/4 |
| 4,655,257 | 4/1987 | Iwashita | 128/4 X |
| 4,659,195 | 4/1987 | D'Amelio et al. | 128/4 X |

Primary Examiner—William H. Grieb

[57] ABSTRACT

An endoscope comprises an operating body and an inserting portion extending therefrom. A distal end section of the inserting portion is formed into a bendable section. An angularly movable member is mounted within the operating body for angular movement around a predetermined axis. The bendable section is operatively connected to the angularly movable member through a pair of operating wires or wire sections. A hydraulic actuator is operatively connected to the angularly movable member. An operating member located exteriorly of the operating body is operatively connected to the angularly movable member. As the operating member is operated to angularly move the angularly movable member around the predetermined axis to bend the bendable section, moment of rotation is applied to the angularly movable member by the hydraulic actuator, to angularly move the angularly movable member around the predetermined axis in the same direction as that in which the angularly movable member is angularly moved around the predetermined axis by the operating member.

28 Claims, 23 Drawing Figures

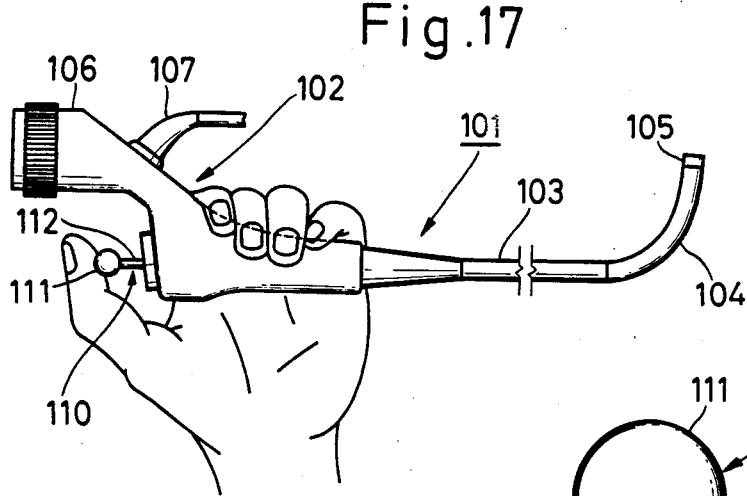
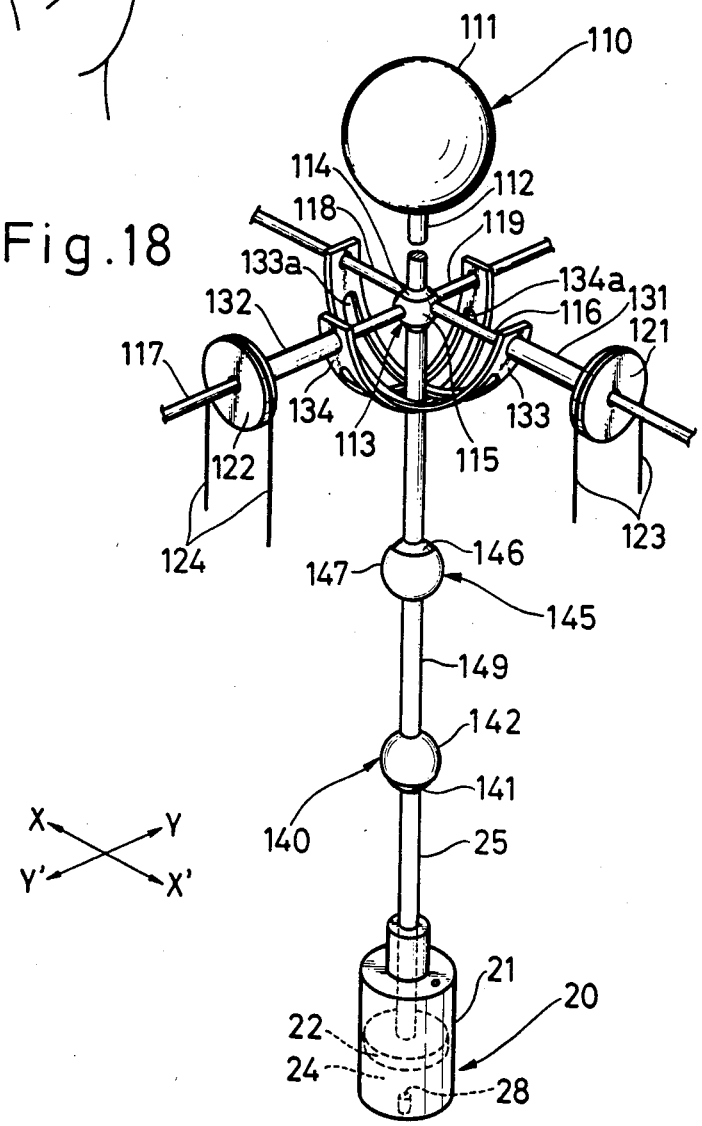

OPERATING MECHANISM FOR BENDABLE SECTION OF ENDOSCOPE

BACKGROUND OF THE INVENTION

The present invention relates to an endoscope comprising an inserting portion insertable into, for example, a body cavity of a subject, an interior of a machine or the like, to perform observation and, more particularly, to an operating mechanism for a bendable section of the inserting portion.

A usual, conventional endoscope comprises an operating body and an inserting portion extending therefrom, in which the inserting portion has a distal end section formed into a bendable section. An angularly movable member such as a pulley or the like is mounted, within the operating body, on a shaft for angular movement therewith around an axis thereof. An operating member such as a lever is connected to an end of the shaft which extends outwardly from the operating body. The angularly movable member is operatively connected to a distal end of the bendable section through a pair of operating wire sections. After insertion of the inserting portion of the endoscope into, for example, a body cavity of a subject by an operator or an operating surgeon, he turns the operating lever to angularly move the angularly movable member around the axis of the shaft. The angular movement of the angularly movable member is transmitted to the bendable section through the operating wire sections to bend the bendable section toward any desired direction.

The construction as described above is somewhat disadvantageous in that as the bending angle of the bendable section increases, the reaction force from the bendable section increases and, therefore, great force is required for the operating surgeon to operate the operating lever to angularly move the angularly movable member, to thereby result in reduction in the operability.

As disclosed in Japanese Patent Publication No. 56-13455 and Japanese Utility Model Application Laid-Open No. 58-160002, an arrangement has been proposed in which an electric motor is utilized as a power source. The electric motor is incorporated into the operating body and is operatively connected to the angularly movable member for angularly moving the same around the axis of the shaft.

With the construction as described above, the operability is reduced, because the incorporation of the electric motor into the operating body increases the weight thereof. In addition, in the event that the failure of electric power supply occurs after the inserting portion has been inserted into the body cavity of the subject and the bendable section has been bent to a desired angle, it is no longer possible to withdraw the inserting portion out of the cavity of the subject, because it is impossible to release the bent condition of the bendable section.

OBJECT AND SUMMARY OF THE INVENTION

An object of the present invention is to provide an endoscope which has an improved operability.

According to the invention, there is provided an endoscope comprising:

(a) an operating body;
(b) an inserting portion extending from the operating body and having a distal end section formed into a bendable section;
(c) at least one angularly movable member mounted within the operating body for angular movement around a predetermined axis;
(d) at least one pair of operating wire means having their respective one ends operatively connected to the angularly movable member and the respective other ends operatively connected to the bendable section;
(e) at least one operating member arranged exteriorly of the operating body;
(f) first connecting means for operatively connecting the angularly movable member and the operating member to each other;
(g) at least one hydraulic actuator means disposed within the operating body and including a cylinder, a piston slidably received in the cylinder and cooperating with the same to define therein a cylinder chamber supplied with a hydraulic pressure, and a piston rod having one end thereof connected to the piston;
(h) second connecting means for operatively connecting the other end of the piston rod of the hydraulic actuator means to the angularly movable member to transmit a force from the hydraulic actuator means to the angularly movable member;
(i) at least one hydraulic pressure source means arranged exteriorly of the operating body; and
(j) at least one passageway means connecting the hydraulic pressure source means and the cylinder chamber of the hydraulic actuator means to each other, for permitting the hydraulic pressure to be supplied from the hydraulic pressure source means into the cylinder chamber.

BRIEF DESCRIPTION OF THE DRAWINGS

FIG. 17 is a side elevational view showing an endoscope in accordance with a thirteenth embodiment of the invention which is capable of bending a bendable section of an inserting portion in any direction by a single operating lever;

FIG. 18 is a fragmental perspective view showing, on an enlarged scale, a mechanism for driving two pairs of operating wire sections, which mechanism is incorporated into the endoscope illustrated in FIG. 17;

DETAILED DESCRIPTION

Figure 1:
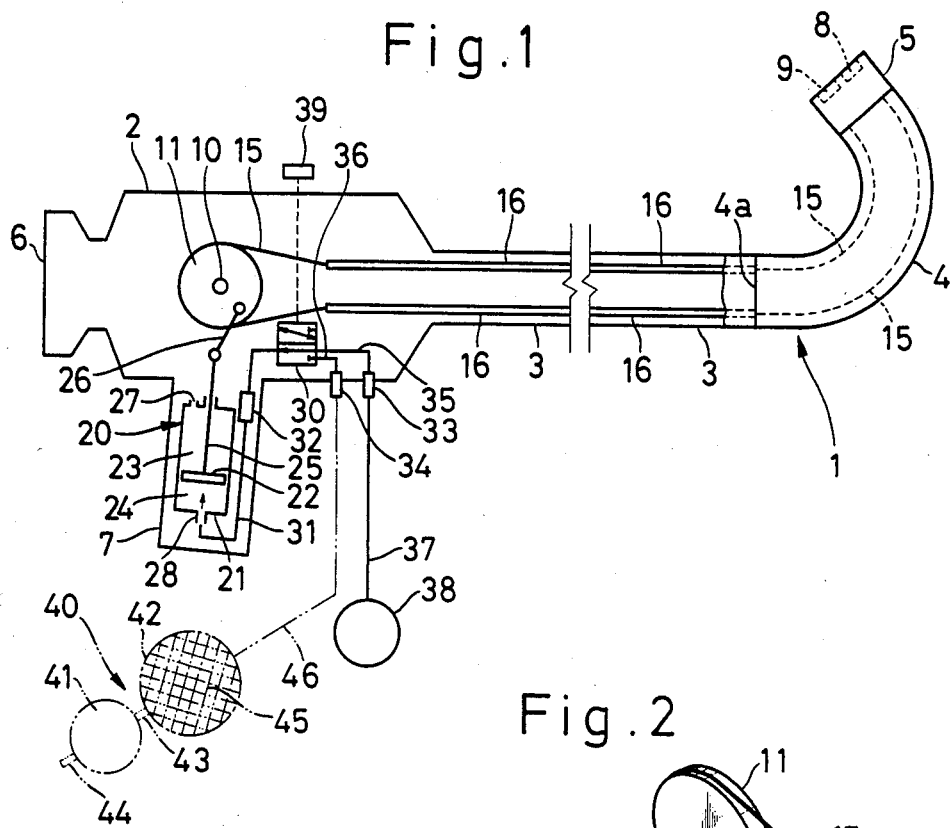
FIG. 1 is a cross-sectional, schematic side elevational view showing an endoscope in accordance with a first embodiment of the invention.

Various embodiments of the invention will now be described with reference to the accompanying drawings in which like reference numerals are used to designate like or similar parts and components.

Figure 2:
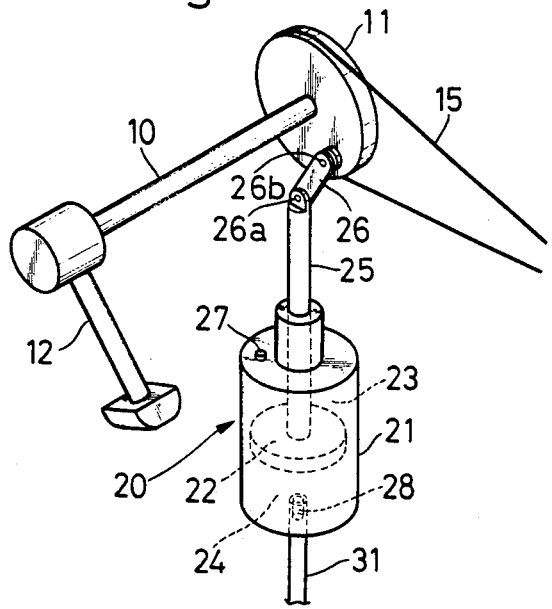
FIG. 2 is a fragmental perspective view showing, on an enlarged scale, a pneumatic actuator schematically illustrated in FIG. 1.

Referring to FIGS. 1 and 2, an endoscope 1 in accordance with a first embodiment of the invention comprises an operating body 2, and a flexible inserting portion 3 extending from a forward end of the operating body 2. The inserting portion 3 has a distal end section formed into a bendable section 4 which has at its distal end a hard or rigid tip component 5. An ocular portion 6 is provided at a rear end of the operating body 2, and a grip portion 7 is provided at lower side of the operating body 2 and projects therefrom outwardly such that a longitudinal axis of the grip portion 7 intersects an extended line of the inserting portion 3. The tip component 5 is provided in an end face thereof with a viewing window 8 and an illuminating window 9. The viewing window 8 is optically connected to the ocular portion 6 through an image transmitting optical system including an optical fiber bundle which extends through the inserting portion 3 and the operating body 2. Another optical fiber bundle having one end thereof optically connected to the illuminating window 9 extends through the inserting portion 3, the operating body 2 and a guide cable (not shown) connected to the operating body 2. The other end of the another optical fiber bundle is optically connected to a light source unit (not shown).

A shaft 10 is mounted in the operating body 2 for angular movement around an axis of the shaft 10 which is located on the extended line of the inserting portion 3 and which extends perpendicularly thereto. A pulley 11 serving as an angularly movable member is fixedly mounted, within the operating body 2, on the shaft 10 for angular movement therewith around a predetermined axis coincident with the axis of the shaft 10. The shaft 10 has one end thereof extending outwardly from the operating body 2, and an operating lever 12 is fixedly connected to the extending one end of the shaft 10, as shown in FIG. 2. Thus, the pulley 11 is connected to the operating lever 12 through the shaft 10.

A single continuous wire has a longitudinally intermediate portion which is trained around the pulley 11 and which is fixedly secured thereto at a single point, so that a pair of operating wire sections 15 and 15 extend respectively from upper and lower sides of the pulley 11 toward the inserting portion 3. The pair of operating wire sections 15 and 15 extend respectively through a pair of helical tubes 16 and 16 within the inserting portion 3. Each helical tube 16 has one end thereof fixedly secured to the operating body 2 and the other end fixedly secured to an end 4a of the bendable section 4 opposite to the tip component 5. Ends of the respective operating wire sections 15 and 15 remote from the pulley 11 are fixedly connected to the tip component 5 at respective locations diametrically opposite to each other, i.e., spaced apart from each other through 180 degrees.

A hydraulic actuator, more particularly, a pneumatic actuator 20 is arranged within the grip portion 7. The actuator 20 comprises a cylinder 21 fixed to the grip portion 7, and a piston 22 slidably received within the cylinder 21 and cooperating with the same to define therein upper and lower cylinder chambers 23 and 24.

A piston rod 25 has one end thereof fixedly connected to the piston 22 and slidably extends through an upper end wall of the cylinder 21. The other end of the piston rod 25 is pivotally connected to one end of a link 26 by means of a pin 26a, and the other end of the link 26 is pivotally connected to a side surface of the pulley 11 by means of a pin 26b. The piston rod 25 has a longitudinal axis thereof extending perpendicularly to the axis of the shaft 10. The upper cylinder chamber 23 is in communication with a space within the operating body 6 through a communication bore 27 provided in the upper end wall of the cylinder 21. A hydraulic pressure supply port 28 is formed in a lower end wall of the cylinder 21.

A selector valve 30 is arranged within the operating body 2. A port on one side of the selector valve 30 is connected to the hydraulic pressure supply port 28 through a tube 31. A regulator valve 32 is provided in the tube 31 for maintaining constant a compressed air pressure introduced into the lower cylinder chamber 24 of the cylinder 21.

Two connectors 33 and 34 are mounted in a lower wall of the operating body 2 and are connected respectively to two ports on the other side of the selector valve 30 through tubes 35 and 36. One of the connectors 33 is connected through a tube 37 to a compressed air source 38 such as pump, reservoir or the like, and the other connector 34 opens to the atmosphere in normal use.

An actuator button 39 is disposed on an upper side of the operating body 2 so as to project therefrom outwardly. The selector valve 30 is selectively actuated by the actuator button 39. Specifically, when the actuator button 30 is not depressed, the selector valve 30 occupies a position where the lower cylinder chamber 24 and the compressed air source 38 are brought into communication with each other to allow the compressed air pressure to be applied to the piston 22. When the actuator button 39 is depressed, the selector valve 30 occupies a position where the communication between the lower cylinder chamber 24 and the compressed air source 38 is interrupted and the lower cylinder chamber 24 is allowed to be brought into communication with the atmosphere through the connector 34.

With the construction as described above, the compressed air from the compressed air source 38 is supplied into the lower cylinder chamber 24 of the cylinder 21 through the tubes 37 and 35, the selector valve 30 and the tube 31, so that the compressed air pressure applies a constant force to the piston 22. Further, the force is transmitted to the pulley 11 through the piston rod 25 and the link 26. With the bendable section 4 extending straight, moment of rotation applied to the pulley 11 by the force of the compressed air is zero, because the link 26 is straight aligned with the piston rod 25 and the extended line of the link 26 intersects the axis of the shaft 10 around which the pulley 11 is angularly movable.

If it is desired to bend the bendable section 4 in the counterclockwise direction as viewed in FIG. 1, an operator or operating surgeon turns the operating lever 12 in the counterclockwise direction to angularly move the pulley 11 in the same direction around the axis of the shaft 10. At this time, the operating surgeon can turn the operating lever 12 with his small force without difficulty with the aid of the force applied to the pulley 11 from the pneumatic actuator 20. More specifically, as the bending angle of the bendable section 4 increases, the reaction force from the bendable section 4 also increases. This results in increase in the moment of rotation tending to angularly move the pulley 11 around the axis of the shaft 10 in the direction opposite to the operating direction in which the pulley 11 is angularly moved by the operating lever 12. However, as the pulley 12 is angularly moved, the moment of rotation applied to the pulley 11 by the compressed air acting on the piston 22 is also increased. Consequently, it is possible for the operating surgeon to anularly move the pulley 11 around the axis of the shaft 10 always with his small force, against the reaction force from the bendable section 4. The moment of rotation applied to the pulley 11 by the compressed air pressure is set to a level always lower than the moment of rotation applied to the pulley 11 by the reaction force from the bendable section 4 and, therefore, the pulley 11 is prevented from being self-propelled without operation of the lever 12 in such a direction as to increase the bending angle of the bendable section 4.

Figure 3:
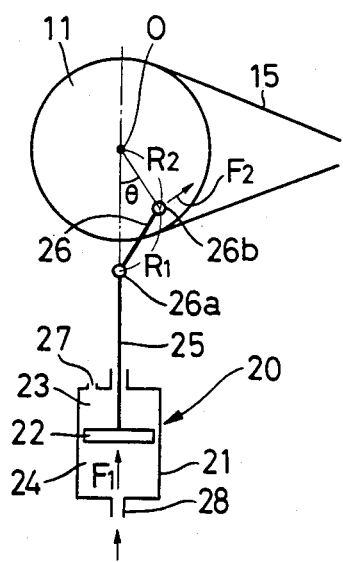
FIG. 3 is a fragmental schematic view for explanation of an action or function of the pneumatic actuator illustrated in FIGS. 1 and 2.
Figure 4:
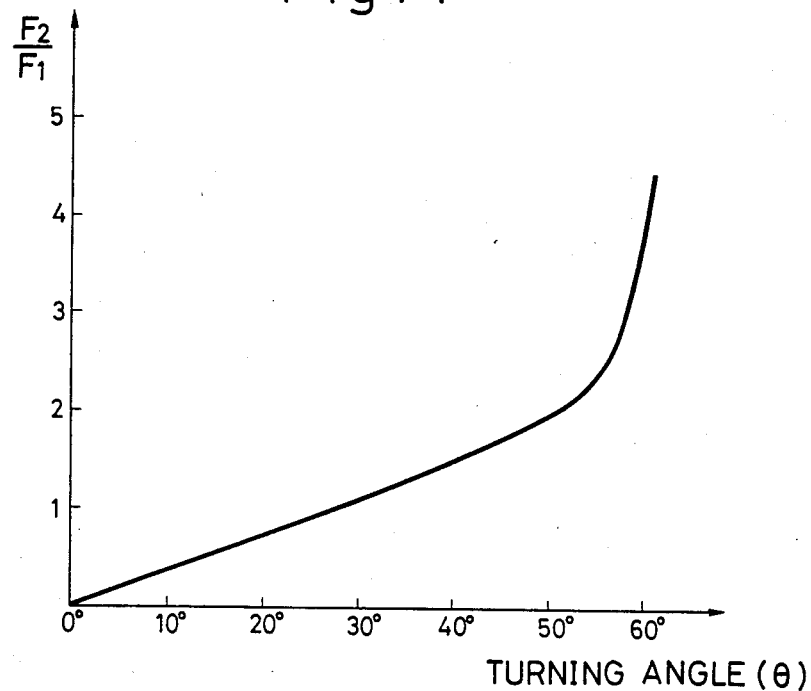
FIG. 4 is a graphical representation of a relationship between a turning angle of a pulley and a turning effect or torque applied to the pulley by the pneumatic actuator shown in FIGS. 1 through 3.

As shown in FIG. 3, assume that a distance between the center of pivotal movement 26a of the link 26 with respect to the piston rod 25 and the center of pivotal movement 26b of the link 26 with respect to the pulley 11 is $R_1$, that a distance between the center of pivotal movement 26b and the center of angular movement 0 of the pulley 11 is $R_2$, that the force applied to the piston 22 by the air pressure is $F_1$, and that, of the force transmitted to the pulley 11 through the link 26, a component tangential to the pulley 11 is $F_2$. Then, $F_2/F_1$ has a relationship shown in FIG. 4 with respect to $R_1/R_2$. The graph of FIG. 4 indicates a case where $R_1/R_2$ is equal to 0.88. As will be seen from FIG. 4, $F_2/F_1$ increases substantially in proportion to the turning angle $\theta$ of the pulley 11 within a range of from 0° to 45°, and as the rotational angle $\theta$ exceeds 45°, $F_2/F_1$ abruptly increases. The curve having such changing rate approximates to a curve of changing rate in the reaction force from the bendable section 4 with respect to the bending angle thereof. Accordingly, by appropriate selection of $R_1/R_2$, the changing rate in $F_2/F_1$ enables the moment of rotation $F_2 \times R_2$ applied to the pulley II by the pneumatic actuator 20 to substantially correspond to the moment of rotation applied to the pulley 11 by the reaction force from the bendable section 4, and to be lowered or reduced to a level lower than the latter moment of rotation always by a constant value. Consequently, it is made possible for the operating surgeon to easily operate the lever 12 with his substantially constant force.

As described above, as the pulley 11 is angularly moved around the axis of the shaft 10, the piston 22 is moved upwardly. During this upward movement of the piston 22, the air within the upper cylinder chamber 23 is discharged into the operating body 2 through the communication bore 27.

In addition, as described above, since the moment of rotation applied to the pulley 11 by the compressed air pressure reduces the moment of rotation applied to the pulley 11 by the reaction force from the bendable section 4, the operating surgeon can maintain the bendable section 4 at any desired angular position, only if he lightly holds the operating lever 12 with his finger. If the reaction force from the bendable section 4 is great, a brake element may be temporarily pressed against the pulley 11 or the like to cause the frictional force to counteract the reaction force.

If it is desired to return the bendable section 4 from the bent position shown in FIG. 1 to the straight position where the bendable section 4 extends straight, the operating surgeon releases his finger from the operating lever 12 or weakens his operating force on the operating lever 12. Then, the bendable section 4 is returned, under its own reaction force, to the straight position, and the piston rod 25 is retracted so that the link 26 is returned to the position where it is straight aligned with the piston rod 25.

Similarly, if it is desired to bend the bendable section 4 in the clockwise direction as viewed in FIG. 1, the operating lever 12 is turned with a small operating force in the clockwise direction.

When the inserting portion 3 of the endoscope 1 is withdrawn from a body cavity of a subject, the actuator button 39 is depressed to actuate the selector valve 30, to thereby interrupt the communication between the compressed air source 38 and the lower cylinder chamber 24 and bring the lower cylinder chamber 24 into communication with the connector 34. This causes the lower cylinder chamber 24 to open to the atmosphere, so that the pneumatic actuator 20 no longer applies any force to the pulley 11. Under such condition, the operating surgeon releases his finger from the operating lever 12 and withdraws the inserting portion 3 out of the body cavity. Incidentally, the lower cylinder chamber 24 may not necessarily be required to open to the atmosphere. In this case, the operating surgeon should slowly withdraw the inserting portion 3 out of the body cavity.

Should the compressed air be not supplied from the compressed air source 38 because of failure of electric power supply or malfunction, the selector valve 30 is actuated by the actuator button 39 in a manner similar to that described above, to interrupt the communication between the compressed air source 38 and the lower cylinder chamber 24 and to bring the latter into communication with the connector 34. Subsequently, a double balloon 40 is connected to the connector 34, as indicated by the phantom lines in FIG. 1. The double balloon 40 is known as one for medical treatment and comprises two rubber bags 41 and 42 connected to each other through a check valve 43. One of the bags 41 is in communication with the atmosphere through another check valve 44, and the other bag 42 is covered with a net 45 for restricting the inflation of the bag 42. A tube 46 has one end thereof connected to the bag 42 and the other end connectable to the connector 34. As the operating surgeon operates with his hand to repeatedly press the one bag 41, the atmospheric air is introduced into the other bag 42 and is compressed therein. The compressed air is supplied from the bag 42 to the lower cylinder chamber 24 through the tube 46, connector 34, tube 36, selector valve 30 and tube 31. This enables the lower cylinder chamber 24 to have any desired pressure.

Figure 5:
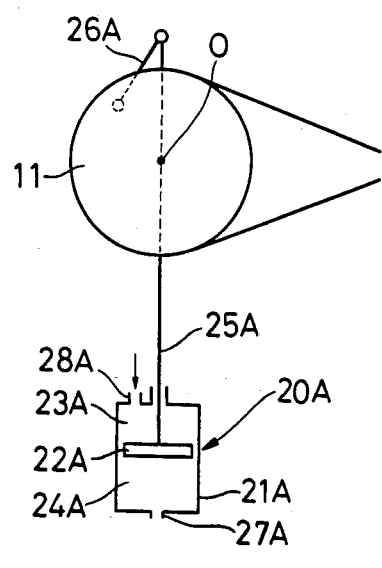
FIG. 5 is a view similar to FIG. 3, but showing second embodiment of the invention comprising a pneumatic actuator which is different, in direction of force acting on the piston, from that shown in FIGS. 1 through 3.

FIG. 5 shows a second embodiment of the invention. In FIG. 5, the same or like reference numerals are used to designate parts or components corresponding to those shown in FIGS. 1 through 3, and the detailed description of such corresponding parts or components will therefore be omitted to avoid duplication. The same is applicable to various other emobiments which will subsequently be described with reference to FIGS. 6 through 23.

In the second embodiment shown in FIG. 5, a pneumatic actuator 20A has a hydraulic pressure supply port 28A formed in an upper end wall of a cylinder 21A, and a communication bore 27A formed in a lower end wall of the cylinder 21A for bringing a lower cylinder chamber 24A into communication with the interior of the operating body. A piston rod 25A is formed so as to have a relatively great length, and intersects the center of angular movement 0 of the pulley 11 at an intermediate portion of the piston rod 25A. A link 26A has opposite ends thereof which are pivotally connected to the forward end of the piston rod 25A and to the side surface of the pulley 11, respectively.

In the second embodiment of FIG. 5, when the bendable section extends straight, the piston rod 25A and the link 26A are overlapped with each other. Similarly to the above-described first emobiment, the compressed air is supplied to an upper cylinder chamber 23A through the hydraulic pressure supply port 28A, to urge the piston 22A downwardly. Thus, the piston rod 25A is subjected to the force in such a direction as to be retracted into the cylinder 21A. As the operating lever is turned to angularly move the pulley 11 around the center of angular movement 0, the link 26A is pivotally moved relatively to the piston rod 25A as shown in FIG. 5, and this causes the force from the piston rod 25A to be converted through the link 26A into the turning effect applied to t he pulley 11. A manner of increase in the turning effect is similar to that of the first embodiment described previously with reference to FIGS. 1 through 3.

Figure 6:
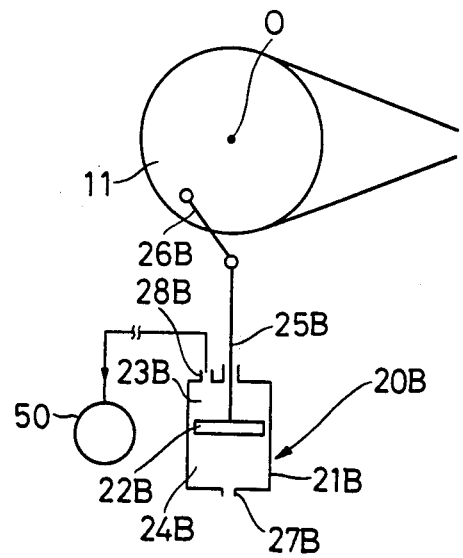
FIG. 6 is a view similar to FIG. 3, but showing a third embodiment of the invention comprising a pneumatic actuator which utilizes negative pressure.

FIG. 6 shows a third embodiment of the invention in which a pneumatic actuator 20B is similar in constructio to the actuator 20A shown in FIG. 5. Specifically, the actuator 20B comprises a hydraulic pressure supply port 28B formed in an upper end wall of a cylinder 21B, and a communication bore 27B formed in a lower end wall of the cylinder 21B for bringing the lower cylinder chamber 24B into communication with the interior of the operating body. However, the piston rod 25B is short in length, like that of the first embodiment shown in FIGS. 1 through 3, and the extended line of the piston rod 25B intersects the center of angular movement 0 of the pulley 11. A link 26B has opposite ends thereof which are pivotally connected to the forward end of the piston rod 25B and to the pulley 11, respectively. A negative pressure source 50 such as suction pump or the like is connected to the hydraulic pressure supply port 28B. In substitution for the compressed air source 38 shown in FIG. 1, the negative pressure source 50 is connected to the connector 34 (FIG. 1).

In the third embodiment shown in FIG. 6, since air is drawn from an upper cylinder chamber 23B through the hydraulic pressure supply port 28B by the negative pressure source 50, a negative pressure is established within the upper cylinder chamber 23B so that the piston 22B is moved upwardly. In other words, the negative pressure is supplied from the negative pressure source 50 to the upper cylinder chamber 23B to actuate the piston 22B. As a result, the piston rod 25B and the link 26B function in a manner similar to that described above in connection with the first embodiment shown in FIGS. 1 through 3.

Figure 7:
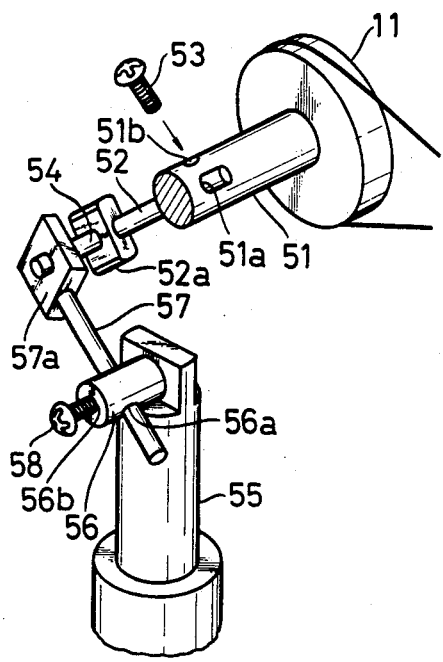
FIG. 7 is a view similar to FIG. 2, but showing a fourth embodiment of the invention which is capable of adjusting a turning effect applied to a pulley by a pneumatic actuator.

FIG. 7 shows a fourth embodiment of the invention in which the pulley 11 is mounted on a sheet 51 for angular movement therewith around an axis thereof. Similarly to the shaft 10 shown in FIG. 2, the shaft 51 has one end thereof extending outwardly from the operating body, and the operating lever (omitted from FIG. 7) is fixedly connected to the extending one end of the shaft 51. A through bore 51a is formed in a portion of the shaft 51 between the pulley 11 and the operating lever and extends perpendiculary to the axis of the shaft 51. A link 52 is inserted in the inserting bore 51a. A threaded bore 51b is also formed in the shaft 51 in perpendicular relation to the inserting bore 51a. A screw 53 threadedly engaged with the threaded bore 51b has a forward end which is pressed against the outer circumferential surface of the link 52, to thereby fixedly secure the link 52a to which one end of a link 54 extending parallel to the shaft 51 is fixedly secured. On the other hand, a short shaft 56 is mounted on a forward end of a piston rod 55 of a pneumatic actuator for angular movement around an axis of the short shaft 56 which extends perpendicularly to the longitudinal axis of the piston rod 55. An inserting bore 56a is formed in the short shaft 56 and extends perpendicularly to the axis thereof, and a link 57 is inserted into the inserting bore 56a. A threaded bore 56b is formed in a forward end face of the short shaft 56 and extends in coaxial relation thereto. A screw 58 is threadedly engaged with the threaded bore 56b and has a forward end pressed against the peripheral surface of the link 57 to fixedly secure the same to the short shaft 56. The link 57 has a planar, wide base 57a through which the aforesaid link 54 extends and in which the link 54 is supported for angular movement around its own axis.

In the forth embodiment shown in FIG. 7, it is possible to vary the inserted and fixed positions of the respective links 52 and 57 with respect to the shafts 51 and 56. That is, it is possible to adjust the length of a portion of the link 52 between the shaft 51 and the link 54 and the length of a portion of the link 57 between the link 54 and the short shaft 56. Consequently, it is possible to adjust the changing rate in the moment of rotation applied to the pulley 11 by the pneumatic actuator, with respect to the turning angle of the pulley 11. Thus, it is possible to adjust the moment or rotation due to penumatic actuator to a level lower, always by a constant value, than the moment of rotation applied to the pulley 11 by the reaction force from the bendable section, correspondly to the changing rate in the moment of rotation due to the reaction force from the bendable section.

Figure 8:
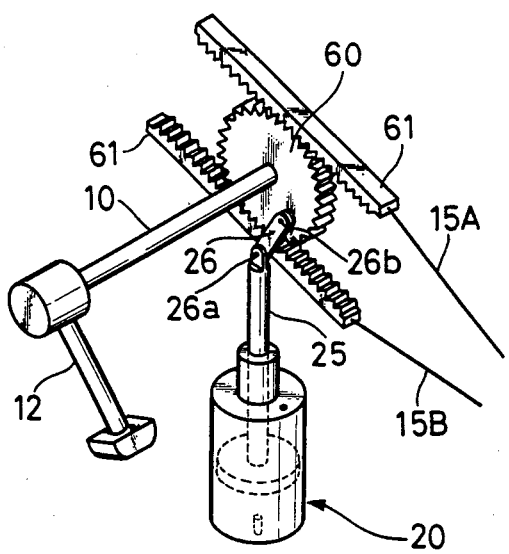
FIG. 8 is a view similar to FIG. 2, but showing a fifth embodiment of the invention which employs a rack and pinion mechanism.

FIG. 8 shows a fifth embodiment of the invention in which a pinion 60 is used, in substitution for the pulley 11 used in the first embodiment shown in FIGS. 1 through 3, as an angularly movable member to which a pair of separate operating wires 15A and 15B are operatively connected. A pair of racks 61 and 61 are in mesh with the pinion 60, and have their respective one ends to which respective one ends of the pair of operating wires 15A and 15B are respectively connected. Each of the racks 61 is supported within the operating body 2 (FIG. 1) by a corresponding guide mechanism (not shown) for sliding movement only in the longitudinal direction. In the fifth embodiment of FIG. 8, the pinion 60 is angularly moved through the shaft 10 around the axis thereof by the operation of the operating lever 12 and is subjected to the mement of rotation due to the force from the pneumatic actuator 20, in a manner similar to that described in connection with the first embodiment shown in FIGS. 1 through 3. The link 26 has opposite ends thereof which are pivotally connected to the forward end of the piston rod 25 and to the side surface of the pinion 60 through the pins 26b and 26a, respectively.

Figure 9:
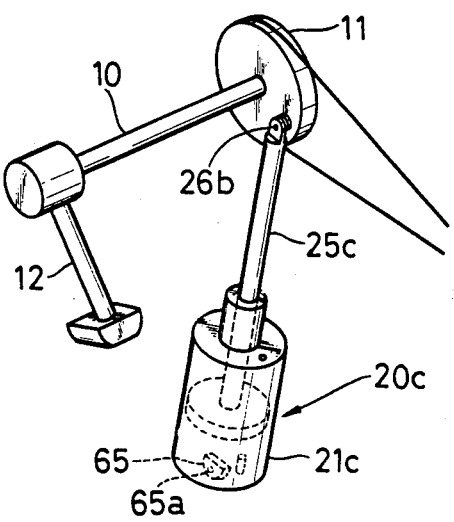
FIG. 9 is a view similar to FIG. 2, but showing a sixth embodiment of the invention in which a pneumatic actuator is pivotally supported on an operating body.

FIG. 9 shows a sixth embodiment of the invention in which a forward end of a piston rod 25C of a pneumatic actuator 20C is pivotally connected directly to the pulley 11 through the pin 26b, without interposition of a link. Further, the pneumatic actuator 20C is supported for pivotal movement relative to the operating body. Specifically, a bracket 65 is fixedly secured to a center of a lower end wall of a cylinder 21C, and a pin (not shown) extending through a bore 65a in the bracket 65 is fixedly secured to the grip portion of the operating body.

In the sixth embodiment shown in FIG. 9, when the bendable section extends straight, the extended line of the piston rod 25C of the pneumatic actuator 20C intersects the center of angular movement of the pulley 11, i.e. the axis of the shaft 10. As the operating lever 12 is operated to angularly move the pulley 11 through the shaft 10 around the axis thereof, the cylinder 21C and the piston rod 25C of the pneumatic actuator 20C are inclined, and the moment of rotation is applied to the pulley 11.

Figure 10:
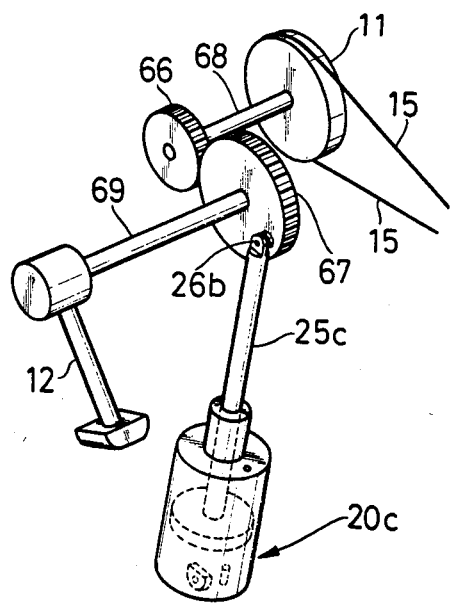
FIG. 10 is a view similar to FIG. 2, but showing a seventh embodiment of the invention which comprises a gear train arranged between a pulley and an operating lever.

FIG. 10 shows a seventh embodiment of the invention in which the pulley 11 is connected to the operating lever 12 through a gear train comprising a small gear 66 and a large gear 67. More specifically, the pulley 11 is fixedly mounted on a shaft 68 for angular movement therewith around an axis thereof. The small gear 66 is fixedly mounted on an end of the shaft 68. The large gear 67 is in mesh with the small gear 66 and is mounted on one end of a shaft 69 for angular movement therewith around an axis thereof extending parallel to the axis of the shaft 68. The operating lever 12 is secured to the other end of the shaft 69. The gear 67 serves as an angularly movable member to which the wire sections 15 and 15 and the operating lever 12 are operatively connected. The forward end of the piston rod 25C of the pneumatic actuator 20C similar to that shown in FIG. 9 is pivotally connected to a side surface of the large gear 67.

In the seventh embodiment shown in FIG. 10, the turning effect from the operating lever 12 is transmitted to the pulley 11 through the shaft 69, gears 67 and 66, and shaft 68. In addition, the force from the pneumatic actuator 20C is converted into a turning effect on the gear 67, and is further transmitted to the pulley 11 through the gear 66 and the shaft 68. The seventh embodiment of FIG. 10 is effective for a case where it is required to increase the bending angle of the bendable section of the endoscope. That is, the use of the gears 66 and 67 enables the bending angle of the bendable section to be increased, without increase in the diameter of the pulley 11 and further while restraining the turning angle of the operating lever 12 at a value within a narrow range.

Figure 11:
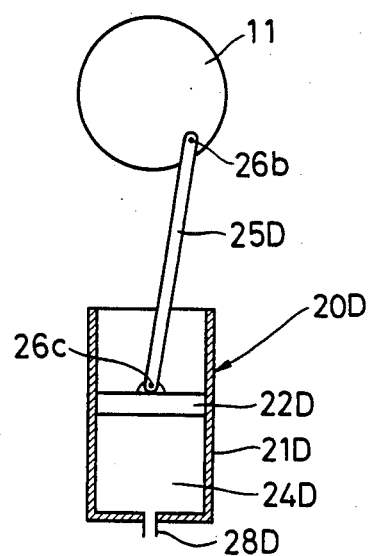
FIG. 11 is a fragmental cross-sectional view showing an eighth embodiment of the invention comprising a pneumatic actuator of a different type in which a piston rod is pivotally connected to a piston.

FIG. 11 shows an eighth embodiment of the invention in which a top end of a cylinder 21D of a pneumatic actuator 20D is open, and the cylinder 21D has a lower end wall provided therein with a hydraulic pressure supply port 28D for introducing the compressed air into a cylinder chamber 24D. In addition, a piston rod 25D has a lower end pivotally connected to a piston 22D by means of a pin 26c, and an upper end pivotally connected to the pulley 11 by means of the pin 26b. In the eighth embodiment, since the lower end of the piston rod 25D is pivotally connected to the piston 22D, it is possible to connect the upper end of the piston rod 25D directly to the pulley 11 without interposition of a link, even if the cylinder 21D is fixedly secured to the grip portion of the operating body so as not to be pivotable.

Figure 12:
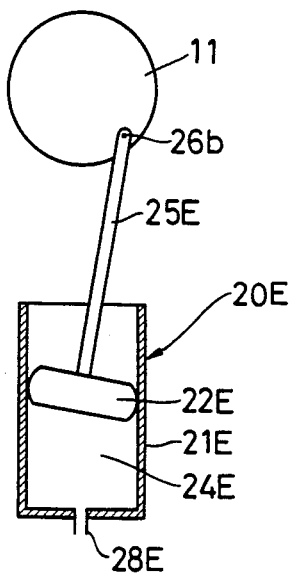
FIG. 12 is a view similar to FIG. 11, but showing a ninth embodiment of the invention comprising a pneumatic actuator in which a piston has a peripheral surface curved in a part-spherical form.

FIG. 12 shows a ninth embodiment of the invention in which a piston 22E of a pneumatic actuator 20E has a peripheral surface curved in a part-spherical form so that the piston 22E is capable of sliding and being inclined with respect to a cylinder 21E. The cylinder 21E has a lower end wall provided therein with a hydraulic pressure supply port 28E for introducing the compressed air into a cylinder chamber 24E. A piston rod 25E has a base end fixedly connected to the piston 22E and a forward end pivotally connected to the pulley 11 through the pin 26b.

In the ninth embodiment shown in FIG. 12, since the piston 22E is capable of being inclined with respect to the cylinder 21E, it is possible to pivotally connect the forward or upper end of the piston rod 25E directly to the pulley 11 without interposition of a link, even if the cylinder 21E is fixedly secured to the grip portion of the operating body so as not to be pivotable.

Figure 13:
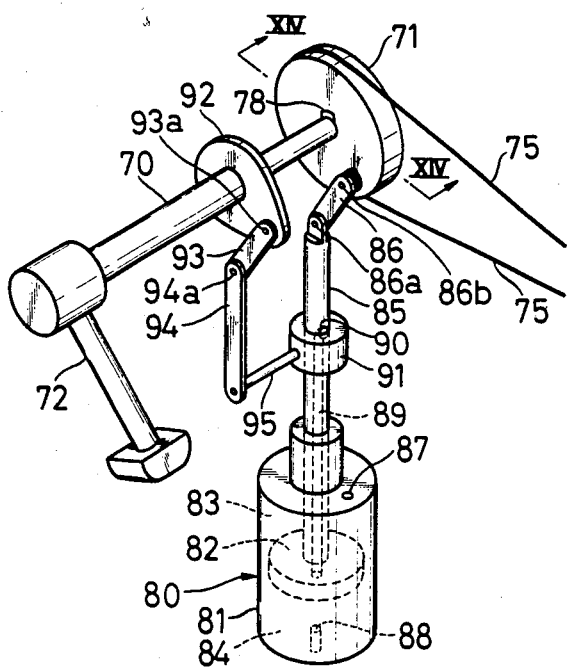
FIG. 13 is a view similar to FIG. 2, but showing a tenth embodiment of the invention in which a pneumatic actuator is actuated by a valve mechanism.
Figure 14:
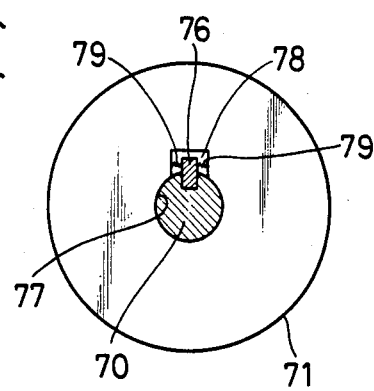
FIG. 14 is an enlarged cross-sectional view taken along the line XIV—XIV of FIG. 13.

FIG. 13 shows a tenth embodiment of the invention in which a pulley 71 is mounted on one end of a shaft 70 which is supported by the operating body for angular movement around the shaft's own axis. The other end of the shaft 70 extends outwardly from the operating body, and an operating lever 72 is fixedly secured to the extending other end of the shaft 70. As shown in FIG. 14, a key 76 is mounted on the one end of the shaft 70 so as to project radially outwardly from the peripheral surface thereof. The pulley 71 is formed therein with an inserting bore 77 through which the shaft 70 extends, and the key 76 is received in a key groove 78 formed in the wall surface of the inserting bore 77. The key groove 78 has a lateral width greater than that of the key 76, and a pair of springs 79 and 79 are disposed respectively between the opposite side surfaces of the key 76 and the opposite side surfaces of the key groove 78. Thus, the shaft 70 is angularly movable around its own axis relatively to the pulley 71 by a play between the key 76 and the key groove 78. The springs 79 and 79 prevent inadvertent or unintentional angular movement or play of the shaft 70 around its own axis relative to the pulley 71, to thereby retain the shaft 70 so as to be located centrally of the key groove 78.

A pneumatic actuator 80 used in the tenth embodiment shown in FIG. 13 comprises, similarly to the first embodiment shown in FIGS. 1 through 3, a cylinder 81 fixedly secured to the operating body, a piston 82 and a piston rod 85. The cylinder 81 has an upper end wall formed therein with a communication bore 87 for bringing an upper cylinder chamber 83 into communication with the interior of the operating body, and a lower end wall provided therein with a hydraulic pressure supply port 88. The piston rod 85 has a longitudinal axis intersecting the axis of the shaft 70. A link 86 has one end thereof pivotally connected to the forward end of the piston rod 85 by means of a pin 86a, and the other end pivotally connected to a side surface of the pulley 71 by means of a pin 86b. A fluid passageway 89 is formed in the piston rod 85 and extends along the longitudinal axis thereof. One end of the fluid passageway 89 extends through the piston 82 and opens to a lower cylinder chamber 84. The other end of the fluid passageway 89 opens at the peripheral surface of the piston rod 85, to form a valve port 90. The valve port 90 is positioned such that it is located exteriorly of the cylinder 81 even though the piston rod 85 occupies any position. The valve port 90 is adapted to be opened and closed by a cylindrical valve member 91 mounted on the piston rod 85 for sliding movement therealong.

A plate-like link 92 is fixedly mounted on the shaft 70. A link 93 has an upper end pivotally connected to an end of the link 92 by means of a pin 93a, and a lower end pivotally connected to an upper end of link 94 by means of a pin 94a. The link 94 has a lower end connected to the aforesaid valve member 91 through a rod-like link 95. The link 94 is guided by a guide mechanism (not shown) arranged within the operating body, so as to be moved longitudinally, i.e., parallel to the piston rod 85, and the extended line of the link 94 intersects the axis of the shaft 70. The aforesaid link 95 extends parallel to the shaft 70.

The distance between the center of pivotal movement 86b of the link 86 with respect to the pulley 71 and the axis of the shaft 70 is made equal to the distance between the center of pivotal movement 93a of the link 93 with respect to the link 92 and the axis of the shaft 70. The distance between the centers of pivotal movement 86a and 86b at the respective ends of the link 86 is made equal to the distance between the centers of pivotal movement 93a and 94a at the respective ends of the link 93.

The longitudinal axis of the piston rod 85 intersects the axis of the shaft 70. When the bendable section extends straight, the piston rod 85 and the link 86 extend in straight aligned relation to each other, and the links 93 and 94 also extend in straight aligned relation to each other. At this time, the valve port 90 of the fluid passageway 89 is disposed so as to be located slightly above the upper end face of the valve member 91. Thus, the valve port 90 is opened, and the compressed air supplied into the lower cylinder chamber 84 is allowed to be discharged from the valve port 90 into the interior of the operating body through the fluid passageway 89. Consequently, the compressed air pressure acting on the piston 82 is extremely low. Moreover, since the piston rod 85 and the link 86 extend in straight aligned relation to each other and the shaft 70 is located on the extended line of the aligned piston rod 85 and link 86, the moment of rotation applied to the pulley 71 is zero so that the piston 82 is maintained stationary and the bendable section is also maintained immovable.

As the operating surgeon slightly turns the operating lever 72 against the resilient force of either end of the springs 79, only the shaft 70 is angularly moved slightly around its own axis, while the pulley 71 is maintained stationary. This results in angular movement of the link 92. The angular movement of the link 92 is converted through the link 93 into an upward rectilinear movement of the link 94, and is further transmitted to the valve member 91. As a result, the valve member 91 is moved upwardly to close the valve port 90. Then, since the compressed air is prevented from escaping through the valve port 90, the piston 82 is subjected to a lifting force by the compressed air. As the operating lever 71 is further turned, the pulley 71 is slightly moved angularly around the axis of the shaft 70 and, consequently, the lifting force acting on the piston 82 is converted through the piston rod 85 and the link 86 into a turning effect applied to the pulley 71. Under such a condition that the pulley 71 is angularly moved around the axis of the shaft 70 through an angle equal to or greater than a predetermined value, the moment of rotation applied to the pulley 71 by the compressed air pressure when the valve port 90 is fully closed is set to a value greater than the moment of rotation applied to the pulley 71 by the reaction force from the bendable section. Consequently, the pulley 71 is angularly moved around the axis of the shaft 70 to pull one of a pair of operating wire sections 75 and 75, to thereby bend the bendable section of the endoscope.

As the operating lever 72 is stopped in turning movement, the valve member 91 stops. However, since the piston 82 is successively subjected to the force due to the air pressure, the piston rod 85 is further slightly moved upwardly and, in due course, the valve port 90 is shifted from the valve member 91 and is opened partially. The compressed air is allowed to escape through a small communication area of the partially opened valve port 90, and the compressed air pressure applied to the piston 82 is reduced.

Accordingly, with the operating surgeon lightly holding the operating lever 72 with his finger against the resilient force of either one of the springs 79 to stop the operating lever 72, the moment of rotation due to the compressed air pressure and the moment of rotation due to the reaction force from the bendable section are balanced with each other at the pulley 71, so that the bendable section is maintained at a predetermined bending angle.

Additionally, if a friction is temporarily applied to the shaft 70, it will be made possible to maintain the bent condition of the bendable section by the aforesaid balance of the moment of rotation, even if the operating surgeon releases his finger from the operating lever 72.

If the operating surgeon continues to turn the operating lever 72 to continuously move the valve member 91 upwardly, the piston rod 85 is moved upwardly, while the valve port 90 has its opening area corresponding to the reaction force from the bendable section. Thus, it is made possible to continuously bend the bendable section 4 (FIG. 1).

In this manner, the operating surgeon can bend the bendable section, if he applies, to the operating lever 72, a small force required to move the valve member 91 upwardly against the resilient force of either one of the springs 79. Thus, the operating surgeon can easily operate the bendable section with his small force.

If it is desired to return the bendable section from the bent condition to the straight condition, it is sufficient if the operating surgeon releases his finger from the operating lever 72. Then, the shaft 70 is angularly moved around its own axis in such a manner that the key 76 is returned to its central position under the action of the pair of springs 79. Consequently, the opening area of the valve port 90 is increased as compared with that when the operating surgeon has lightly held the operating lever 72 with his finger as described previously. This results in decrease in the moment of rotation due to the compressed air pressure as compared with the moment of rotation due to the reaction force from the bendable section. As a result, the bendable section is returned to its straight condition.

Figure 15:
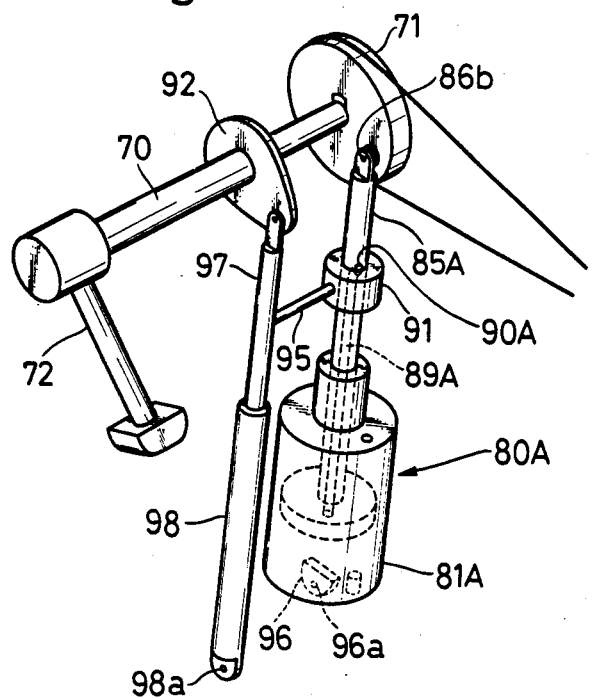
FIG. 15 is a view similar to FIG. 2, but showing an eleventh embodiment of the invention in which a pneumatic actuator actuated by a valve mechanism is pivotally supported on an operating body.

FIG. 15 shows an eleventh embodiment of the invention which is sililar to the tenth embodiment shown in FIG. 13 except that a piston rod 85A of a pneumatic actuator 80A has a forward end which is pivotally connected directly to the pulley 71 through the pin 86b, without interposition of a link. The piston rod 85A is formed therein with a fluid passageway 89A having one end thereof serving as a valve port 90A. A cylinder 81A of the pneumatic actuator 80A is supported for pivotal movement relative to the operating body. That is, a bracket 96 is fixedly secured to a center of a lower end wall of the cylinder 81A, and a pin (not shown) fixedly secured to the grip portion of the operating body extends through a bore 96a in the bracket 96 so as to permit the pivotal movement of the cylinder 81A. The link 92 has the end thereof to which an upper end of a long link 97 is pivotally connected. The link 97 is slidably received within a guide tube 98 in a telescopic manner. The above-described pin, which extends through the bore 96a in the bracket 96, extends through a bore 98a in a lower end of the guide tube 98. The link 97 has an intermediate portion which is connected to the valve member 91 through the link 95.

In the eleventh embodiment shown in FIG. 15, when the bendable section extends straight, the piston rod 85A, guide tube 98 and link 97 extend parallel to each other, and their respective extended lines intersect the axis of the shaft 70. As the operating lever 72 is turned to angularly move the pulley 71 through the shaft 70 around the axis thereof, the piston rod 85A of the pneumatic actuator 80A is moved upwardly while the cylinder 81A and the piston rod 85A are inclined, and the link 97 is also moved upwardly while being inclined at the same angle as the piston rod 85A. Thus, the moment of rotation is applied to the pulley 71.

Figure 16:
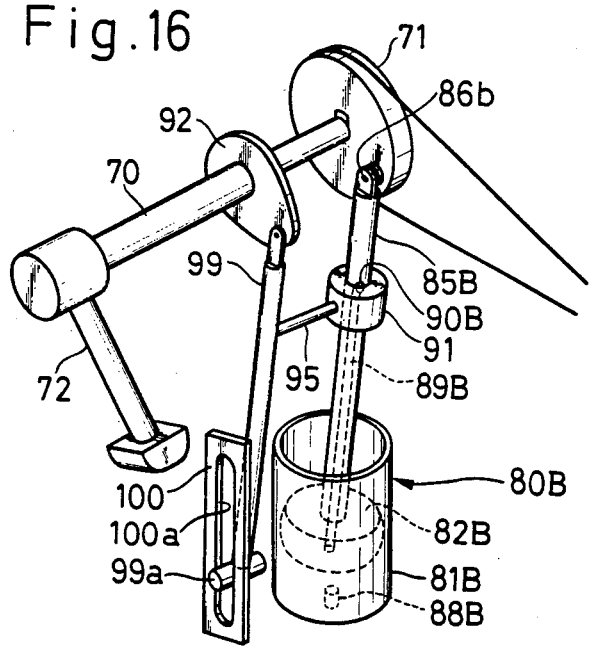
FIG. 16 is a view similar to FIG. 2, but showing a twelfth embodiment of the invention in which a pneumatic actuator actuated by a valve mechanism comprises a piston having a peripheral surface curved in a part-spherical form.

FIG. 16 shows a twelfth embodiment of the invention in which a cylinder 81B of a pneumatic actuator 80B has an upper open end, and a lower end wall of the cylinder 81B is provided therein with a hydraulic pressure supply port 88B. A piston 82B has a peripheral surface curved in a part-spherical form so that the piston 82B is capable of sliding and being inclined relatively to the cylinder 81B. A piston rod 85B has a lower end fixedly secured to the piston 82B, and an upper end pivotally connected to the pulley 71 by means of the pin 86b. The piston rod 85B is formed therein with a fluid passageway 98B having one end thereof serving as a valve port 90B, similarly to the eleventh embodiment shown in FIG. 13. A long link 99 has an upper end pivotally connected to the end of the link 92 fixedly mounted on the shaft 70. An intermediate portion of the link 99 is connected to the valve member 91 through the link 95. A stub or pin 99a is fixedly secured to a lower end of the link 99, and is slidably fitted in an elongated slot 100a in a guide plate 100 which is fixedly mounted within the operating body. The pin 99a is angularly movable around its own axis and slidable along the slot 100a.

In the twelfth embodiment shown in FIG. 16, the turning operation of the operating lever 72 causes the piston rod 85B and the link 99 to be moved upwardly while being inclined at the same angle.

FIGS. 17 and 18 show an endoscope in accordance with a thirteenth embodiment of the invention, which is different from the above-described various embodiments in a driving mechanism for wire sections. Basic structure and arrangement of the driving mechanism are known from Japanese Utility Model application laid-open No. 56-48241. The endoscope 101 comprises an operating body 102 and a flexible inserting portion 103 extending from a forward end of the operating body 102. The inserting portion 103 has a distal end section formed into a bendable section 104 which has, at its forward or distal end, a hard or rigid tip component 105. The tip component 105 has an end face which is provided therein with a viewing window and an illuminating window (both not shown). An ocular portion 106 is provided at an upper rear end of the operating body 102. An optical fiber bundle for transmitting an illuminating light is housed in a guide cable 107 which has one end thereof connected to the upper rear end of the operating body 102. An operating lever 110 is disposed on a lower rear end of the operating body 102 at a location on the extended line of the inserting portion 103.

The operating lever 110 is comprised of a grip 111 and a lever rod 112, with the grip 111 projecting from the operating body 102. As shown in FIG. 18, the lever rod 112 has an intermediate portion which is supported on the operating body 102 through a universal joint 113 disposed therewithin, so that the lever rod 112 can be pivotally moved in any direction around the universal joint 113. More specifically, the universal joint 113 is comprised of a ball portion 114 formed on the intermediate section of the lever rod 112, and a spherical shell 115 surrounding the ball portion 114 and having both open ends. The spherical shell 115 of the universal joint 113 is supported on the operating body 102 through four shafts 116, 117, 118 and 119 circumferentially equidistantly spaced apart from each other around the lever rod 112. The shafts 116 and 118 are arranged so as to extend in the direction X—X' in FIG. 18, i.e., perpendicularly to the drawing sheet in FIG. 17, and the shafts 117 and 119 are arranged so as to extend in the direction Y—Y' in FIG. 18, i.e., vertically in FIG. 17.

Pulleys 121 and 122 each serving as an angularly movable member are mounted respectively on the adjacent shafts 116 and 117 for angular movement around respective axes thereof.

A single continuous wire is trained around the pulley 121 and is fixedly secured thereto at a single location to form a pair of operating wire sections 123 and 123. Similarly, a single continuous wire is trained around the pulley 122 and is fixedly secured thereto at a single location to form a pair of operating wire section 124 and 124. The pair of wire sections 123 and 123 have their respective one ends connected to the tip component 105 at respective locations spaced apart from each other through 180 degrees, i.e., diametrically opposite to each other. The pair of wire sections 124 and 124 have their respective one ends connected to the tip component 105 at respective locations which are shifted through 90 degrees respectively from the connecting locations of the respective wire sections 123 and 123.

Sleeves 131 and 132, through which the shafts 116 and 117 respectively extend, have their respective one ends fixedly connected respectively to side surfaces of the respective pulleys 121 and 122. Arcuate members 133 and 134 have their respective one ends fixedly connected to the other ends of the respective sleeves 131 and 132. The arcuate members 133 and 134 are arranged so as to extend perpendicularly to each other. The arcuate member 133 has opposite ends thereof which are rotatably supported respectively on the shafts 116 and 118. Similarly, the arcuate member 134 has opposite ends thereof which are rotatably supported respectively on the shafts 117 and 119. The arcuate member 133 is formed therein with an elongated slot 133a extending therealong, and the arcuate member 134 is formed therein with an elongated slot 134a extending therealong and intersecting the slot 133a. The lever rod 112 of the operating lever 110 extend through the slots 133a and 134a.

The same pneumatic actuator as that used in the first embodiment shown in FIGS. 1 through 3 is arranged within the operating body 102 at a location on the extended line of the inserting portion 103. Component parts of the pneumatic actuator 20 shown in FIG. 18 are designated by the same reference numerals as those used in FIGS. 1 through 3, and the detailed description of such component parts will be omitted. In the thirteenth embodiment shown in FIGS. 17 and 18, the forward end of the piston rod 25 is operatively connected to the forward end of the lever rod 112 through universal joints 140 and 145 and a link 149. The universal joint 140 is comprised of a ball portion 141 formed at the forward end of the piston rod 141, and a spherical shell 142 fixedly connected to one end of the link 149 and having open one end. The universal joint 145 is comprised of a ball portion 146 formed at the forward end of the lever rod 112 and a spherical shell 147 fixedly connected to the other end of the link 149 and having open one end. The aforesaid universal joint 113 is located on the extended line of the piston rod 25.

With the construction as described above, the compressed air is supplied under constant pressure to the cylinder chamber 24 within the cylinder 21 through the hydraulic pressure supply port 28, and the piston 22 is subjected to a constant force due to the compressed air pressure. When the bendable section 104 extends straight, the piston rod 25, link 149 and lever rod 112 are arranged in straight aligned relation to each other, so that the moment of rotation applied to each of the pulleys 121 and 122 is zero.

In FIG. 17, when it is desired to bend the bendable section 104, the operating surgeon pivotally moves the operating lever 110 around the universal joint 113 in any desired direction. The amount of displacement of the lever rod 112 at this time is divided into a component in the direction X—X' and a component in the direction Y—Y' in FIG. 18. The arcuate members 133 and 134 are angularly moved around the shafts 116 and 118 and the shafts 117 and 119, respectively, correspondingly to the components in the respective directions. As a result, the pulleys 121 and 122 are angularly moved around the axes of the respective shafts 116 and 117, and the bendable section 104 is bent in the desired direction through the operating wire sections 123 and 124.

When the lever rod 112 is pivotally moved around the universal joint 113 as described above, the lever rod 112 and the link 149 are bent at the universal joint 145. At this time, the force applied to the piston rod 25 by the compressed air pressure acts to further bend the lever rod 112 and the link 149 at the universal joint 145. In other words, the force due to the compressed air pressure acts in such a direction as to turn the lever rod 112 in the direction in which the lever rod 112 is operated to be turned. As a result, the moment of rotation due to the compressed air pressure is applied to the pulleys 121 and 122 through the respective arcuate members 133 and 134 and the respective sleeves 131 and 132. Thus, it is possible for the operating surgeon to easily operate the operating lever 110 with his small force with the aid of the force due to the compressed air pressure. As the bending angle of the bendable section 104 increases, the reaction force from the bendable section 104 also increases. This results in increase in the moment of rotation tending to angularly move the pulleys 121 and 122 around the respective axes of the shafts 116 and 117 in respective directions opposite to the directions in which the pulleys 121 and 122 are angularly moved by the operation of the operating lever 110. However, since the moment of rotation applied to the pulleys 121 and 122 due to the compressed air pressure also increases, it is possible for the operating surgeon to angularly move the pulleys 121 and 122 always with his small force against the reaction force from the bendable section 104.

In addition, since the moment of rotation due to the compressed air pressure is set to a value always lower than the moment of rotation due to the reaction force from the bendable section 104, the pulleys 121 and 122 are prevented from being self-propelled in such a direction as to increase the bending angle of the bendable section 104, without operation of the operating lever 110.

When it is desired to return the bendable section 104 from the bent condition shown in FIG. 17 to the straight condition, the operating surgeon releases his finger from the operating lever 110, or weakens his operating force on the operating lever 110. Then, the bendable section 104 is returned, under its own reaction force, to the initial straight condition.

Figure 19:
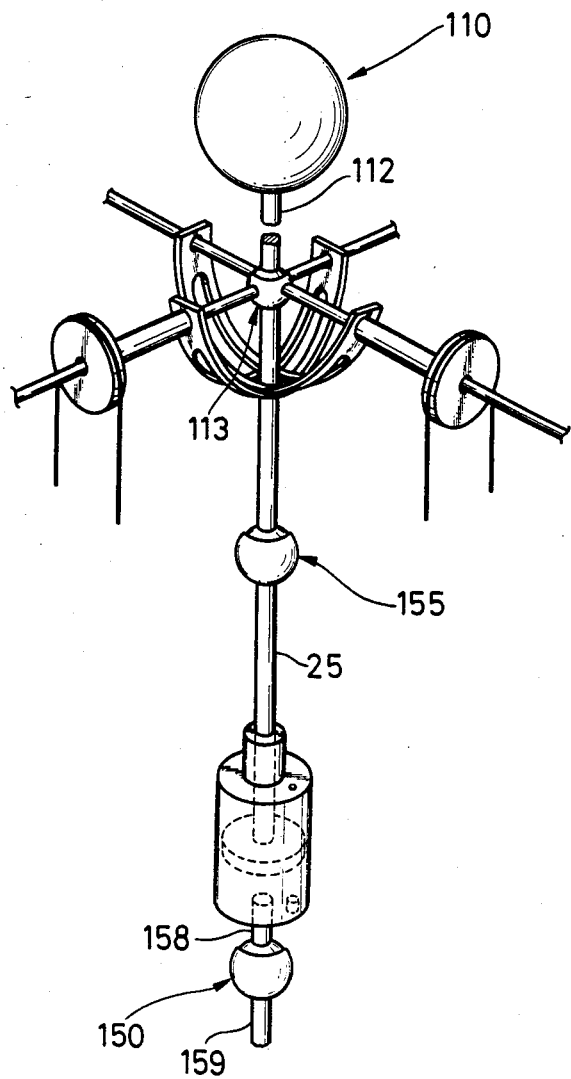
FIG. 19 is a view similar to FIG. 18, but showing a fourteenth embodiment of the invention comprising a wire driving mechanism which includes a pneumatic actuator pivotally supported on an operating body.

FIG. 19 shows a fourteenth embodiment of the invention which comprises a driving mechanism for two pairs of operating wire sections, modified from that used in the endoscope 101 shown in FIG. 17. A support shaft 158 has one end thereof fixedly connected to a center of the lower end wall of the cylinder 21 of the pneumatic actuator 20. The other end of the support shaft 158 is connected to one end of a support shaft 159 through a universal joint 158. The other end of the support shaft 159 is fixedly secured to the operating body 102 (FIG. 17). Thus, the cylinder 21 is pivotally supported on the operating body. Further, the forward end of the piston rod 25 is directly connected to the forward end of the lever rod 112 of the operating lever 110 through a universal joint 155. With the construction shown in FIG. 19, as the operating lever 110 is angularly moved around the universal joint 113, the lever rod 112 and the piston rod 25 are bent at the universal joint 155.

Figure 20:
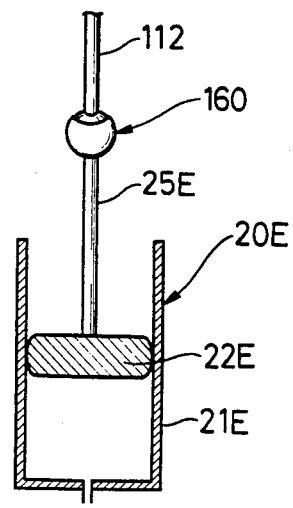
FIG. 20 is a fragmental cross-sectional view showing a fifteenth embodiment of the invention in which a piston of a pneumatic actuator has a peripheral surface curved in a part-spherical form.

FIG. 20 shows a fifteenth embodiment of the invention which utilizes a pneumatic actuator 20E similar to that shown in FIG. 12, in substitution for the pneumatic actuator 20 used in the thirteenth embodiment shown in FIGS. 17 and 18. The cylinder 21E having an upper open end is fixedly secured to the operating body 102 (FIG. 17). The piston 22E having a peripheral surface curved in a part-spherical form is received in the cylinder 21E for sliding movement and pivotal movement relative thereto. The piston rod 25E has the base end fixedly secured to the piston 22E, and the forward end directly connected to the forward end of the lever rod 112 through a universal joint 160.

Figure 21:
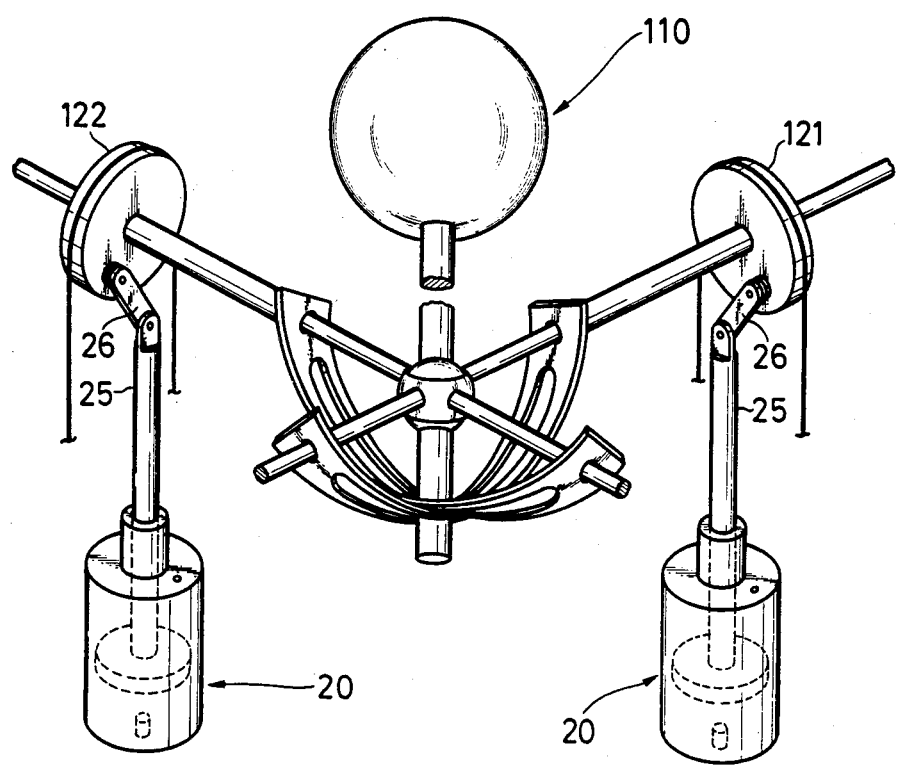
FIG. 21 is a view silimar to FIG. 18, but showing a sixteenth embodiment of the invention comprising a wire driving mechanism which includes two pneumatic actuators connected respectively to pulleys.

FIG. 21 shows a sixteenth embodiment of the invention in which a driving mechanism for two pairs of operating wire sections is basically identical with that used in the thirteenth embodiment shown in FIGS. 17 and 18, but two pneumatic actuators 20 and 20 are used as an auxiliary power, each pneumatic actuator 20 being similar in construction to that incorporated into the first embodiment shown in FIGS. 1 through 3. The piston rod 25 of each of the pneumatic actuators 20 is connected to the side surface of a corresponding one of the pulleys 121 and 122 through a corresponding one of the links 26. The sixteenth embodiment shown in FIG. 21 is similar to the thirteenth embodiment shown in FIGS. 17 and 18 in the action or function angularly moving the pulleys 121 and 122 by the operating lever 110, and is similar to the first embodiment shown in FIGS. 1 through 3 in the action or function applying the moment of rotation to the pulleys 121 and 122 by the respective pneumatic actuators 20 and 20.

Figure 22:
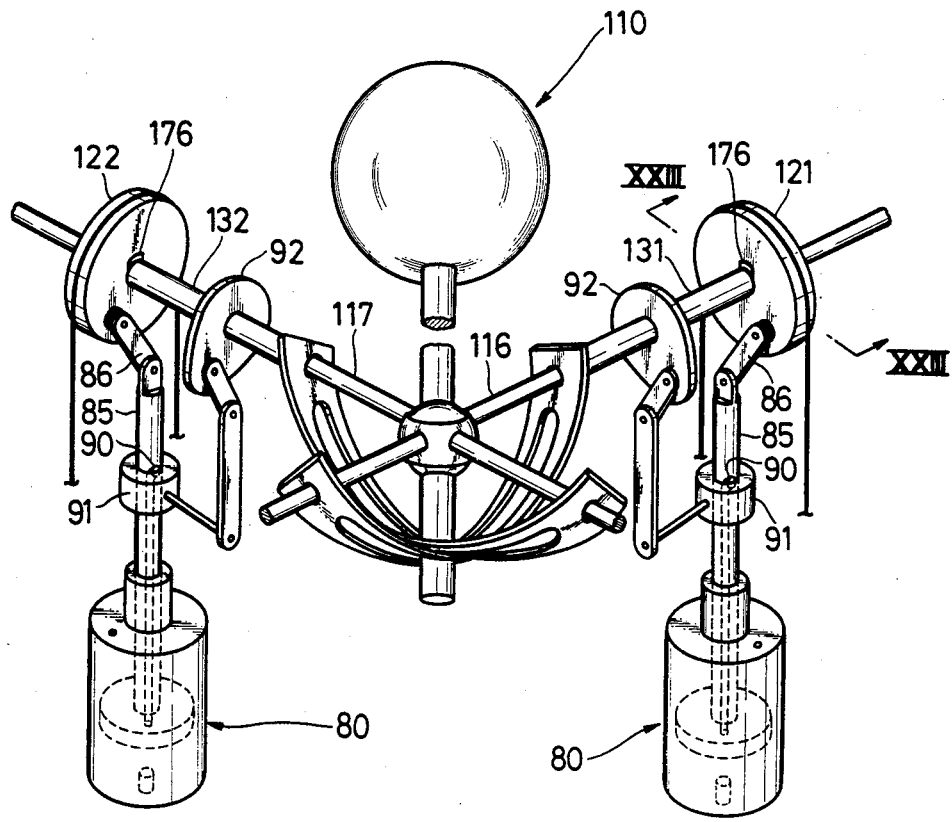
FIG. 22 is a view similar to FIG. 18, but showing a seventeenth embodiment of the invention in which two pneumatic actuators actuated respectively by valve mechanisms are connected respectively to pulleys.
Figure 23:
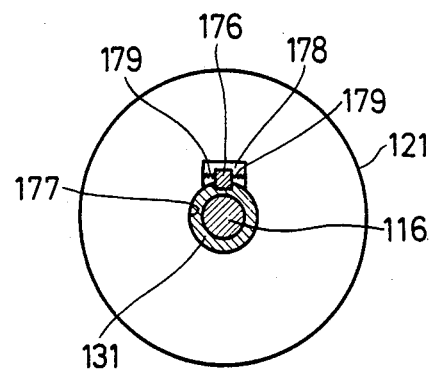
FIG. 23 is an enlarged cross-sectional view taken along the line XXIII—XXIII of FIG. 22.

FIG. 22 shows a seventeenth embodiment of the invention in which a driving mechanism for two pairs of operating wires is basically identical with that used in the thirteenth embodiment shown in FIGS. 17 and 18, but two pneumatic actuators 80 and 80 are used as an auxiliary power, each actuator 80 being similar in construction to that incorporated into the tenth embodiment shown in FIGS. 13 and 14. The piston rod 85 of each of the pneumatic actuators 80 is connected to the side surface of a corresponding one of the pulleys 121 and 122 through a corresponding one of the links 86. Means for operatively connecting the operating lever 110 to each of the valve members 91 for opening and closing a corresponding one of the valve ports 90 comprises a corresponding one of the links 92 which is fixedly mounted on a corresponding one of the sleeves 131 and 132 which, in turn, is rotatably supported on a corresponding one of the shafts 116 and 117. Only the means for operatively connecting the operating lever 110 to the valve member 91 through the link 92 fixedly mounted on the sleeve 131 will be described with reference to FIGS. 22 and 23, but the means for operatively connecting the operating lever 110 to the valve member 91 through the link 92 fixedly mounted on the sleeve 132 will not be described because of similar construction. As shown in FIG. 23, a key 176 is fixedly mounted on the sleeve 131, and the pulley 121 is formed therein with an inserting bore 177 through which the sleeve 131 extends. A key groove 178 in which the key 176 is received is formed in the wall surface of the inserting bore 177 in the pulley 121. The key groove 178 has a lateral width greater than that of the key 176, and a pair of springs 179 and 179 are disposed respectively between the opposite side surfaces of the key 176 and the opposite side surfaces of the key groove 178. Thus, the sleeve 131 is angularly movable around its own axis relatively to the pulley 121 by a play between the key 176 and the key groove 178. The springs 179 and 179 retain the sleeve 131 so as to be located centrally of the key groove 178.

The seventeenth embodiment shown in FIGS. 22 and 23 is similar to the thirteeenth embodiment shown in FIGS. 17 and 18 in the action or function angularly moving the pulleys 121 and 122 by the operating lever 110, and is similar to the tenth embodiment shown in FIGS. 13 and 14 in the action or function applying the moment of rotation to the pulleys 121 and 122 by the respective pneumatic actuators 80 and 80.

The present invention should not be limited to the specific embodiments described above, but various changes and modifications can be made to the embodiments. For example, the arrangement as shown in FIG. 6 in which the pneumatic actuator is actuated by the negative pressure, is applicable to the fourth to seventeenth embodiments shown in FIGS. 7 through 23.

An operating member has been described as being comprised of the operating lever, but may be comprised of an operating dial.

Working fluid for the hydraulic actuator has been described as being air, but may be liquid such as water, oil or the like.

Each of the first to twelfth embodiments shown in FIGS. 1 through 16 has been described as having a single pulley or pinion so that the bendable section is curved in a single plane, but the bendable section may be curved in two planes perpendicular to each other. In this case, another set of a pair of operating wires or wire sections, an angularly movable member and an operating member in necessary, and two hydraulic actuators are operatively connected respectively to the angularly movable members.

In each of the first to twelfth embodiments shown in FIGS. 1 through 16, the operating body may not be provided with the grip portion. In this case, the piston rod of the hydraulic actuator is disposed at a location on the extended line of the inserting portion.

The arrangement comprising the racks and the pinion as shown in FIG. 8 or the arrangement comprising the gear train as shown in FIG. 10 is applicable to each of the tenth to seventeenth embodiments shown in FIGS. 13 through 23.

In each of the thirteenth to seventeenth embodiments shown in FIGS. 17 through 23, three pulleys and three pairs of operating wire sections may be arranged in circumferentially equidistantly spaced relation to each other around the lever rod.

In each of the tenth and seventeenth embodiments shown respectively in FIGS. 13 and 14 and FIGS. 22 and 23, the moment of rotation applied to the angularly movable member due to the hydraulic pressure when the valve port is fully closed may be set to a value lower than that applied to the angularly movable member by the reaction force from the bendable section.

What is claimed is:

1. An endoscope comprising:
   (a) an operating body;
   (b) an inserting portion extending from said operating body and having a distal end section formed into a bendable section;
   (c) at least one angularly movable member mounted within said operating body for angular movement around a predetermined axis;
   (d) at least one pair of operating wire means having their respective one ends operatively connected to said angularly movable member and the respective other ends operatively connected to said bendable section;
   (e) at least one operating member arranged exteriorly of said operating body;
   (f) first connecting means for operatively connecting said angularly movable member and said operating member to each other;
   (g) at least one hydraulic actuator means disposed within said operating body and including a cylinder, a piston slidably received in said cylinder and cooperating with the same to define therein a cylinder chamber supplied with a hydraulic pressure, and a piston rod having one end thereof connected to said piston;
   (h) second connecting means for operatively connecting the other end of said piston rod of said hydraulic actuator means to said angularly movable member to transmit a force from said hydraulic actuator means to said angularly movable member;
   (i) at least one hydraulic pressure source means arranged exteriorly of said operating body;
   (j) at least one passageway means connecting said hydraulic pressure source means and said cylinder chamber of said hydraulic actuator means to each other, for permitting the hydraulic pressure to be supplied from said hydraulic pressure source means into said cylinder chamber.

2. An endoscope as defined in claim 1, wherein said angularly movable member comprises a pulley, and said pair of operating wire means comprise a single continuous wire traind around said pulley and fixedly secured thereto to form a pair of operating wire sections constituting said pair of operating wire means.

3. An endoscope as defined in claim 1, including:
   said angularly movable member comprising a pinion; and
   a pair of racks in mesh with said pinion, the respective one ends of said pair of operating wire means being connected respectively to said pair of racks.

4. An endoscope as defined in claim 1, wherein said first connecting means comprises a shaft mounted in said operating body for angular movement around the shaft's own axis and having one end extending outwardly from said operating body, said angularly movable member being mounted, within said operating body, on said shaft for angular movement therewith around said predetermined axis coincident with the axis of said shaft, said operating member being connected to the extending one end of said shaft.

5. An endoscope as defined in claim 1, wherein said first connecting means comprises a first shaft mounted in said operating body for angular movement around the first shaft's own axis, said angularly movable member being mounted on said first shaft for angular movement therewith around said predetermined axis coincident with the axis of said first shaft, a second shaft mounted in said operating body for angular movement around the second shaft's own axis and having one end extending outwardly from said operating body, said operating member being connected to the extending one end of said second shaft, and a gear train interposed between said first and second shafts.

6. An endoscope as defined in claim 5, wherein said gear train comprises a small gear and a large gear in mesh with said small gear, said small gear being connected to said first shaft, and said large gear being connected to said second shaft.

7. An endoscope as defined in claim 6, wherein the other end of said piston rod of said hydraulic actuator means is operatively connected to one of said small and large gears of said gear train.

8. An endoscope as defined in claim 1, wherein said second connecting means comprises a link having one end thereof pivotally connected to the other end of said piston rod, the other end of said link being pivotally connected to a side surface of said angularly movable member, said cylinder of said hydraulic actuator means being fixedly secured to said operating body, said piston rod having a longitudinal axis intersecting said predetermined axis, said link and said piston rod being arranged in straight aligned relation to each other when said bendable section extends straight.

9. An endoscope as defined in claim 1, wherein said second connecting means comprises a first shaft mounted in said operating body for angular movement around the first shaft's own axis and having one end extending outwardly from said operating body, said angularly movable member being mounted on said first shaft for angular movement therewith around said predetermined axis coincident with the axis of said first shaft, said operating member being connected to the extending one end of said first shaft, a first inserting bore formed in said first shaft and having an axis extending perpendicularly to the axis of said first shaft, a first link inserted into said first inserting bore, a screw screwed into said first shaft for fixing said first link thereto, a second shaft connected to the other end of said piston rod for angular movement around the second shaft's own axis, a second inserting bore formed in said second shaft, a second link inserted into said second inserting bore, and a screw screwed into said second shaft for fixing said second link thereto, said first and second links being connected to each other for angular movement around a common axis relative to each other.

10. An endoscope as defined in claim 9, wherein the axis of said first shaft, the axis of said second shaft, and said common axis extend in parallel relation to each other.

11. An endoscope as defined in claim 1, wherein said second connecting means comprises a pin, the other end of said piston rod being pivotally connected directly to a side surface of said angularly movable member through said pin, said piston rod having a longitudinal axis thereof intersecting said predetermined axis when said bendable section extends straight.

12. An endoscope as defined in claim 11, including:
   means for pivotally supporting said cylinder of said hydraulic actuator means on said operating body, said cylinder and said piston rod being capable of being inclined as said angularly movable member is angularly moved around said predetermined axis.

13. An endoscope as defined in claim 11, wherein the one end of said piston rod is pivotally connected to said piston.

14. An endoscope as defined in claim 11, wherein said piston has a peripheral surface curved in a part-spherical form so that said piston is capable of sliding and being inclined relatively to said cylinder.

15. An endoscope as defined in claim 1, including:
first and second angularly movable members;
first and second pairs of operating wire means associated respectively with said first and second angularly movable members;
said operating member comprising an operating lever;
said first connecting means comprising a universal joint disposed within said operating body for supporting said operating lever pivotally around said universal joint, four shafts arranged within said operating body in circumferentially equidistantly spaced apart from each other around said universal joint, for fixing said universal joint with respect to said operating body, two sleeves mounted respectively on adjacent two of said shafts for angular movement around axes of the respective shafts, said sleeves having their respective one ends connected respectively to said first and second angularly movable members, and two arcuate members each having opposite ends thereof respectively supported on corresponding two of said shafts arranged in straight aligned relation to each other, one of the opposite ends of each of said arcuate members being connected to the other end of a corresponding one of said sleeves; and
each of said arcuate members being formed therein with an elongated slot, said arcuate members intersecting each other, said operating lever extending through the elongated slots in the respective arcuate members.

16. An endoscope as defined in claim 15, wherein said second connecting means comprises a link, and second and third universal joints, and wherein said operating lever has one end thereof disposed within said operating body and the other end extending outwardly from said operating body, the other end of said piston rod of said hydraulic actuator means being connected to one end of said link through said second universal joint, the other end of said link being connected to the one end of said operating lever through said third universal joint, said piston rod and said operating lever being arranged in straight aligned relation to each other when said bendable section extend straight.

17. An endoscope as defined in claim 15, including:
second and third universal joints;
said operating lever having one end thereof disposed within said operating body and the other end extending outwardly from said operating body;
the other end of said piston rod of said hydraulic actuator means being connected to the one end of said operating lever through said second universal joint;
said cylinder of said hydraulic actuator means being connected to said operating body through said third universal joint; and
said piston rod and said operating lever being arranged in straight aligned relation to each other when said bendable section extends straight.

18. An endoscope as defined in claim 15, including:
a second universal joint;
said operating lever having one end thereof disposed within said operating body and the other end extending outwardly from said operating body;
said piston of said hydraulic actuator means having a peripheral surface curved in a part-spherical form so that said piston is capable of sliding and being inclined with respect to said cylinder; and
the one end of said piston rod being fixedly secured to said piston, and the other end of said piston rod being connected to the one end of said operating lever through said second universal joint.

19. An endoscope as defined in claim 15, including:
first and second hydraulic actuator means operatively connected respectively to said first and second angularly movable members.

20. An endoscope as defined in claim 1, including:
fluid passageway means formed in said piston rod of said hydraulic actuator means and extending axially of said piston rod, said fluid passageway means having one end thereof opening to said cylinder chamber and the other end opening to a peripheral surface of said piston rod outside said cylinder to form a valve port;
a valve member mounted on said piston rod for sliding movement therealong, for opening and closing said valve port; and
third connecting means for operatively connecting said operating member and said valve member to each other.

21. An endoscope as defined in claim 20 wherein said first connecting means comprises an elongated member mounted on said operating body for angular movement around the elongated member's own axis, said angularly movable member being mounted on said elongated member for angular movement therewith around said predetermined axis coincident with the longitudinal axis of said elongated member, said operating member being operatively connected to said elongated member, said angularly movable member being formed therein with an inserting bore extending along said predetermined axis, said elongated member being inserted into said inserting bore, said first connecting means further comprising a key fixedly mounted on a portion of said elongated member which is located in said inserting bore, a key groove formed in a wall surface of said inserting bore in said angularly movable member for receiving said key, said key groove having a width greater than that of said key to provide a play therebetween, and springs disposed respectively between opposite side surfaces of said key groove and opposite side surfaces of said key.

22. An endoscope as defined in claim 21, wherein said second connecting means comprises a link having one end thereof pivotally connected to the other end of said piston rod and the other end pivotally connected to a side surface of said angularly movable member, and wherein said third connecting means comprises a first link fixedly mounted on said elongated members, a second link having one end thereof pivotally connected to said first link, a third link having one end thereof connected to the other end of said second link, and a fourth link for connecting the other end of said third link to said valve member, said second link being pivotally moved in parallel relation to said link of said second connecting means, said third link extending parallel to said piston rod and movable longitudinally thereof, and said fourth link extending in parallel relation to said elongated member and being movable toward and away from said elongated member.

23. An endoscope as defined in claim 21, including:
means for pivotally supporting said cylinder of said hydraulic actuator means on said operating body, said cylinder and said piston rod being capable of being inclined with respect to said operating body as said angularly movable member is angularly moved around said predetermined axis; and
said third connecting means comprising a first link fixedly mounted on said elongated member, a second link having one end thereof pivotally connected to said first link, a guide tube pivotally connected to said operating body and slidably receiving said second link, and a third link connecting an intermediate portion of said second link to said valve member, said second link and said guide tube being capable of being inclined in parallel relation to said piston rod.

24. An endoscope as defined in claim 21, wherein said piston has a peripheral surface curved in a part-spherical form and is capable of sliding and being inclined with respect to said cylinder, and wherein said third connecting means comprises a first link fixedly mounted on said elongated member, a second link having one end thereof pivotally connected to said first link, a pin provided on the other end of said second link, and a guide plate fixedly secured to said operating body and having an elongated slot, said pin on said second link being slidably fitted in said elongated slot, said second link being capable of being inclined in parallel relation to said piston rod.

25. An endoscope as defined in claim 1, wherein said hydraulic actuator means comprises a pneumatic actuator, and said hydraulic pressure source means comprises a compressed air source, said cylinder chamber of said pneumatic actuator being connected to said compressed air source by said passageway means.

26. An endoscope as defined in claim 1, wherein said hydraulic actuator means comprises a pneumatic actuator, and said hydraulic pressure source means comprises a negative pressure supply source, said cylinder chamber of said pneumatic actuator being connected to said negative pressure supply source by said passageway means.

27. An endoscope as defined in claim 1, wherein said operating body has a grip portion having an axis extending in such a direction as to intersect an extended line of said inserting portion, said hydraulic actuator means being received within said grip portion.

28. An endoscope as defined in claim 1, including:
said passageway means comprising a first connector mounted on said operating body;
a second connector mounted on said operating body and having one end opening to the atmosphere;
a valve disposed within said operating body and provided in said passageway means, the other end of said second connector being connected to said valve, said valve being capable of occupying a first position where said hydraulic pressure source means is brought into communication with said cylinder chamber through said passageway means and a second position where the communication between said hydraulic pressure source means and said cylinder chamber is interrupted and the cylinder chamber is brought into communication with the atmosphere through said second connector; and
an actuator button disposed exteriorly of said operating body for actuating said valve between said first and second positions.

* * * * *